(12) United States Patent
Ueda

(10) Patent No.: US 6,550,961 B1
(45) Date of Patent: Apr. 22, 2003

(54) THERMAL CONDUCTIVITY DETECTOR

(75) Inventor: Masahito Ueda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/697,059

(22) Filed: Oct. 26, 2000

(30) Foreign Application Priority Data

Dec. 17, 1999 (JP) .......................................... 11-358830

(51) Int. Cl.[7] .......................... G01N 25/00; G01N 30/04
(52) U.S. Cl. ...................... 374/44; 73/23.35; 73/23.39; 95/87; 96/102
(58) Field of Search ........................... 731/23.35, 23.39, 731/23.4; 422/67, 96; 374/43, 44; 95/87; 96/101, 102

(56) References Cited

U.S. PATENT DOCUMENTS

| | | | | |
|---|---|---|---|---|
| 4,088,458 A | * | 5/1978 | Jourdan ........................ | 55/197 |
| 4,509,855 A | * | 4/1985 | Gay ............................. | 356/72 |
| 4,594,879 A | * | 6/1986 | Maeda et al. ................ | 73/27 R |
| 4,741,198 A | * | 5/1988 | Farren et al. ................ | 73/23.1 |
| 4,929,089 A | * | 5/1990 | Tsuchida ..................... | 374/44 |
| 5,031,126 A | * | 7/1991 | McCulloch et al. ........ | 364/557 |
| 5,711,604 A | * | 1/1998 | Nakamura ................... | 374/44 |
| 5,756,878 A | * | 5/1998 | Muto et al. ................. | 73/25.03 |
| 5,772,321 A | * | 6/1998 | Rhodes ........................ | 374/44 |
| 6,062,065 A | * | 5/2000 | Sugimoto et al. .......... | 73/23.42 |
| 6,205,841 B1 | * | 3/2001 | Shibamoto .................. | 73/23.41 |
| 2001/0007224 A1 | * | 7/2001 | Wilson ........................ | 96/4 |

* cited by examiner

*Primary Examiner*—Diego Gutierrez
*Assistant Examiner*—Gail Verbitsky
(74) *Attorney, Agent, or Firm*—Beyer Weaver & Thomas LLP

(57) ABSTRACT

A thermal conductivity detector includes not only a thermal conductivity detector cell disposed so as to be heated by heat transmitted from a first heater block and a column connector connected to the detector cell and to a column of a chromatograph but also a second heater block for heating the column connector. The heaters for individually heating these two heater blocks are controlled simultaneously and in synchronism by a single temperature controller according to the temperature of the first heater block for heating the detector cell.

10 Claims, 1 Drawing Sheet

THERMAL CONDUCTIVITY DETECTOR

BACKGROUND OF THE INVENTION

This invention relates to a thermal conductivity detector for a gas chromatograph.

The thermal conductivity detector is the oldest detector which has been used with a chromatograph. If a filament is set in the flow of a gas streaming out of a column and is kept under a heated condition by applying a constant voltage or a constant current, the temperature of the filament changes in response to a change in the composition of the gas because its thermal conductivity is thereby affected. The thermal conductivity detector is structured so as to detect a change in the electric resistance of such a filament caused by a change in its thermal conductivity by converting the change in the resistance into that of voltage and detecting this voltage change by means of a bridge circuit.

Since the thermal conductivity detector is adapted to detect a change in the composition of a gas or its concentration by detecting a change in temperature, it must be designed such that there would be as little temperature changes as possible due to causes other than the composition or the concentration of the gas. Thus, efforts have been made to eliminate the variations in the source voltage not only by using a heater to control the temperature of the thermal conductivity detector cell inclusive of the filament and surrounding it with a thermal insulator so as to eliminate the environmental temperature effects but also by using a constant current source or a constant voltage source for the filament. It has been known, furthermore, to provide two mutually parallel flow routes within the same cell such that a differential output from the filaments inside these flow routes can be detected.

FIG. 2 shows an example of such a prior art thermal conductivity detector cell 1 comprising a metallic block, say, of a stainless steel material, having two gas flow routes 11 (only one of them being shown in FIG. 2) therethrough. Each gas flow route 11 contains a filament 2, and a carrier gas containing sample components from a column 8 of a gas chromatograph flows through one of the flow routes (the "sample flow route") while the other flow route (the "reference flow route") is adapted to pass only the carrier gas supplied thereto from another column (not shown) of the same kind and size as the column 8 of the gas chromatograph, serving only to provide a flow resistance. The arrows in FIG. 2 show the direction of the gas flow.

A cylindrically shaped heater block 3 with a heater 4 buried inside is intimately in contact with the detector cell 1. The heater 4 has a heater line sealed inside a metallic cylinder through an electrically insulating heat-resistant material. A thermally sensitive resistor serving as a temperature sensor 5 is provided near its surface, and the electric power to be supplied to the heater 4 is controlled by a temperature controller 6 according to a signal received from the temperature sensor 5.

As the temperature near the surface of the heater 4 is thus adjusted to a specified level, the heater block 3 also comes to have about the same temperature, being made of a metal having a high thermal conductivity. Moreover, the detector cell 1 also comes to be of the specified temperature, and both the detector cell 1 and the heater block 3 (inclusive of the heater 4 and the temperature sensor 5 contained therein) are wrapped by a thermally insulating material (not shown) and are thereby thermally insulated from the environment and protected from the effects of the surrounding temperature or the wind.

The column 8 is inside another thermostatic container referred to as the column oven 9, having its temperature controlled by another temperature controlling device (not shown). The column 8 is connected through a joint 81 to a column connector 7 facing the interior of the column oven 9. The column connector 7 is connected to the detector cell 1 through a metallic pipe 71. The structure described above is the same for both of the flow routes in order to maintain a thermal balance between the column 8 and the detector cell 1.

With a prior art detector structured as described above, the temperature of the heater block 3 may change in an oscillatory manner as the power to the heater 4 is switched on and off in order to control its temperature. Such temperature fluctuations are likely to appear as a noise for the detector. In order to minimize such a noise, it has been a common practice to make the heater block 3 substantially larger than the detector cell 1 in size such that the heater block 3 with a larger heat capacity can substantially absorb the temperature variations and its oscillatory changes can be smoothed out. If the heat capacity of the heater block 3 is thus made larger, however, it takes a longer time to raise its temperature. In other words, when the gas chromatograph is started from its original cooled condition, the wait time (or the so-called stabilization time) required for the temperature of the detector to become sufficiently high such that an analysis can be started becomes too long.

If the thermal capacity of the heater block 3 is reduced carelessly in order to shorten the stabilization time, there appears the danger of oscillatory temperature changes, as explained above. In view of this problem, there have been system improvements such as by introduction of a computer for controlling the temperature. Even if the problem of oscillatory temperature variations of the heater is overcome by such means, however, there still remains another problem related to the effects of heat transmitted from the column oven 9. In other words, since the column connector 7 penetrates into the interior of the column oven 9 and is hence directly exposed to the temperature of the column oven 9, its heat is easily transmitted through the metallic tube 71 to the detector cell 1 and disturbs its thermally stabilized condition. A conventional method of avoiding this phenomenon has been to arrange the metallic tube 71 so as to intimately contact the heater block 3 in the middle such that the heat from the oven 9 will be absorbed by the heater block 3 before reaching the detector cell 1. If the heater block 3 is made smaller, however, it can no longer function as a heat sink to effectively absorb the heat from the oven 9. In other words, the detector cell 1 becomes susceptible once again to the oven temperature.

An attempt has been made, in view of the above, to provide the column connector 7 with another heater block having another heater buried therein and to control its temperature. This method is not satisfactory because an additional component for its temperature control becomes necessary and it affects the overall production cost adversely. In addition, there will be an additional problem of oscillatory temperature changes caused as this additional heater is switched on and off, giving rise to the trouble of an increase in the noise.

SUMMARY OF THE INVENTION

It is therefore an object of this invention in view of the problems described above, to provide an improved thermal conductivity detector having a short stabilization time.

It is a particular object of this invention to provide such a thermal conductivity detector capable of reducing the ill-effects of heat from a column oven by reducing the heat capacity of its temperature control system.

A thermal conductivity detector embodying this invention, with which the above and other objects can be accomplished, may be characterized as comprising not only a thermal conductivity detector cell disposed so as to be heated by heat transmitted from a heater block but also an additional heater block for heating the column connector through which the detector cell is connected to a column of a chromatograph. The heaters for individually heating these two heater blocks are controlled simultaneously and in synchronism by a single temperature controller according to the temperature of the first heater block for heating the detector cell. With a detector thus structured, the column connector is heated by a separate heater such that its temperature is controlled simultaneously with the detector cell to be kept nearly constant. Thus, even if the a heater block for the detector cell is made smaller and its heat capacity is reduced, the effect of the temperature of the column oven on the detector cell can be minimized and the stabilization time at the start-up of a chromatographic analysis can be made shorter by reducing the heat capacity of the temperature control system for the detector.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings.

Throughout herein, those components which are substantially identical or at least similar to each other are indicated by the same symbols and may not necessarily be explained in detail for the convenience of description.

DETAILED DESCRIPTION OF THE INVENTION

Figure 1:
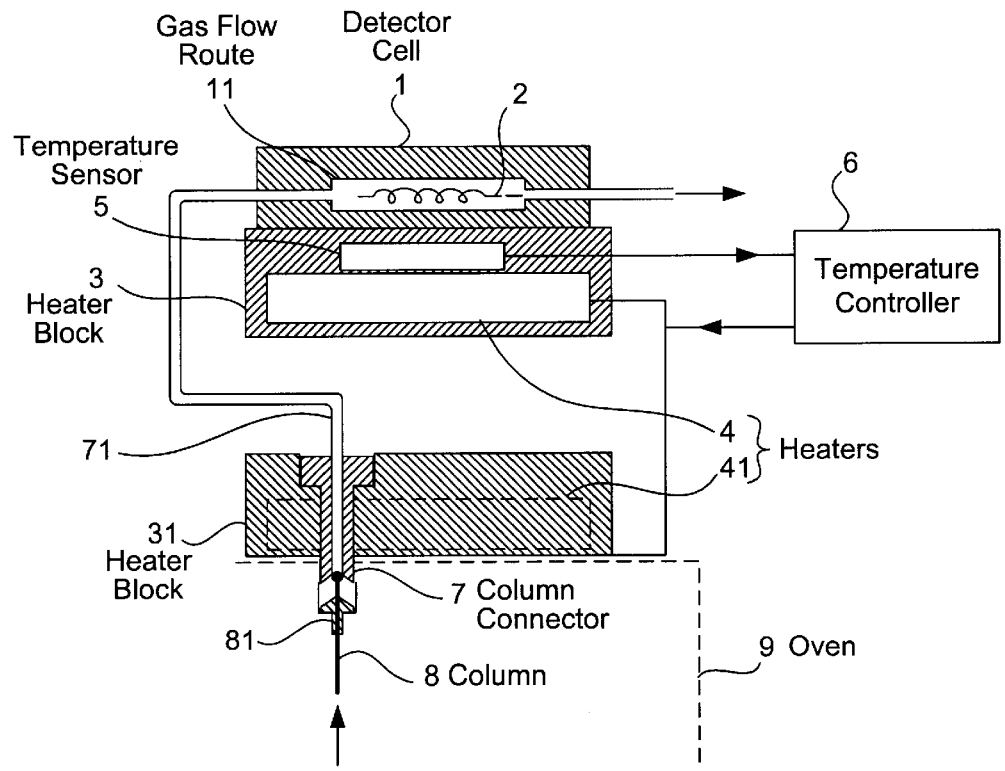
FIG. 1 is a block diagram of a thermal conductivity detector embodying this invention.
Figure 2:
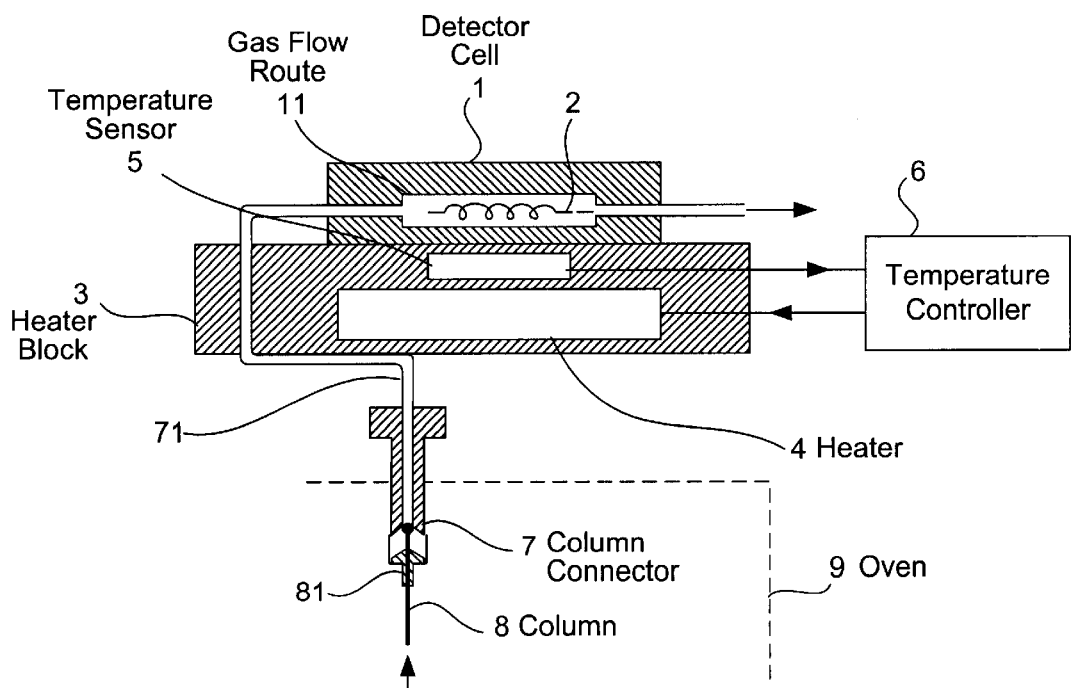
FIG. 2 is a block diagram of a prior art thermal conductivity detector.

The invention is described next by way of an example with reference to FIG. 1 which shows a thermal conductivity detector (herein abbreviated into "TCD") embodying this invention. For the convenience of description, those of the components which are substantially identical, or at least similar, to each other between FIGS. 1 and 2 will be indicated by the same symbols and may not necessarily be explained in detail.

The TCD embodying this invention and shown in FIG. 1 is different from the prior art TCD described above with reference to FIG. 1 firstly in that its heater block 3 (herein referred to as the "first heater block") is smaller such that its heat capacity is about the same as that of its TCD cell 1 and hence will have a shorter stabilization time. Another difference is that there is additionally provided a second heater block 31 shaped similarly to and having the same heat capacity as the first heater block 3. The second heater block 31 also contains a heater 41 for heating it and also the column connector 7 attached to the second heater block 31. The two heaters 4 and 41 have the same power output capacity (say, in units of watts) and are controlled simultaneously by a same temperature controller 6.

Only a tip portion of the column connector 7 is inside the column oven 9 in order to be connected to the column 8 but the column connector 7 is mostly inside the second heater block 31 and is maintained at the same temperature as the second heater block 31. The second heater block 31 is covered by a thermally insulating material (not shown) so as not to be affected by the environmental temperature, and in particular by the heat from the column oven 9. There is no temperature sensor provided to the second heater block 31, and its heater 41 is connected in parallel with the heater 4 inside the first heater block 3 and equal power is supplied to it and to the heater 4 of the first heater block 3 in synchronism with the temperature control on the first heater block 3. Because the first and second heater blocks 3 and 31 are similarly shaped, have about the same heat capacity, and receive power equally, they are maintained at about the same temperature. As a result, the column connector 7 is maintained at about the same temperature as the TCD cell 1, and hence it is possible to obviate the problem of the heat from the column oven 9 reaching the TCD cell 1 through the column connector 7 and the metallic tube 71. Since the temperature of the second heater block 31 is controlled similarly to that of the first heater block 3, furthermore, it is also possible to obviate the danger of oscillatory changes of its temperature becoming a new source of noise for the TCD cell 1.

Although the invention has been described above by way of only one example, this example is not intended to limit the scope of the invention. Many modifications and variations are possible within the scope of this invention. The two heater blocks 3 and 31, for example, need not have exactly the same heat capacity or the same shape, nor is it essential that the two heaters 4 and 41 for heating them have the same power output capacity, as long as the two heater blocks 3 and 31 can be maintained approximately at the same temperature. As another example, the heat capacity of the first heater block 3 need not be equal to that of the TCD cell 1. The present invention is applicable even if the heat capacity of the first heater block 3 is as large as that of the prior art TCD described above with reference to FIG. 2 because the effect of heat from the column oven can be reduced and hence a stabler baseline can be obtained in the case of an analysis by increasing the temperature. Moreover, the two heaters 4 and 41 need not be connected in parallel with each other. What is important is that power can be supplied to both heaters simultaneously from a single temperature controller. If the resistance values of these heaters are selected appropriately, they may be connected in series and a similar desirable result can still be obtained.

What is claimed is:

1. A thermal conductivity detector comprising:
   a thermal conductivity detector cell;
   a column connector connected to said thermal conductivity detector cell for connecting to a column of a chromatograph;
   a first heater block for heating said thermal conductivity detector cell;
   a first heater for heating said first heater block;
   a temperature sensor for sensing temperature of said first heater block;
   a second heater block disposed for heating said column connector;
   a second heater for heating said second heater block; and
   a temperature controller for controlling power supplied to said first heater and to said second heater simultaneously in synchronism according to temperature of said first heater block.

2. The thermal conductivity detector of claim 1 wherein said temperature controller controls power supplied to said first heater according to signals received from said temperature sensor.

3. The thermal conductivity detector of claim 1 wherein said first heater and said second heater are connected in parallel with respect to each other.

4. The thermal conductivity detector of claim 1 wherein power output capacities of said first heater and said second heater are equal.

5. The thermal conductivity detector of claim 3 wherein power output capacities of said first heater and said second heater are equal.

6. The thermal conductivity detector of claim 1 wherein heat capacities of said first heater block and said second heater block are nearly equal.

7. The thermal conductivity detector of claim 4 wherein heat capacities of said first heater block and said second heater block are nearly equal.

8. The thermal conductivity detector of claim 5 wherein heat capacities of said first heater block and said second heater block are nearly equal.

9. The thermal conductivity detector of claim 1 wherein heat capacities of said first heater and said thermal conductivity detector cell are nearly equal.

10. The thermal conductivity detector of claim 1 wherein said thermal conductivity detector cell includes a filament and a gas flow route connected to said column and serves to measure changes in thermal conductivity of a gas flowing through said gas flow route from said column by detecting changes in resistivity of said filament.

* * * * *